United States Patent
Tanaka et al.

(10) Patent No.: US 6,613,735 B2
(45) Date of Patent: *Sep. 2, 2003

(54) COMPOSITION FOR POLYPEPTIDE TRANSFER TO CELLS

(75) Inventors: Kenichi Tanaka, Niigata (JP); Hiroshi Kikuchi, Tokyo (JP); Norio Suzuki, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/032,546

(22) Filed: Jan. 2, 2002

(65) Prior Publication Data

US 2002/0111326 A1 Aug. 15, 2002

Related U.S. Application Data

(62) Division of application No. 09/402,452, filed as application No. PCT/JP98/00685 on Feb. 19, 1998, now Pat. No. 6,372,714.

(30) Foreign Application Priority Data

Apr. 7, 1997 (JP) .............................................. 9-088546
Apr. 7, 1997 (JP) .............................................. 9-088547

(51) Int. Cl.$^7$ .............................................. A61K 38/00
(52) U.S. Cl. .......................... 514/2; 424/422; 424/428; 424/449; 424/450; 264/4.1
(58) Field of Search .............................. 514/2; 424/450, 424/422, 428, 449; 264/4.1

(56) References Cited

U.S. PATENT DOCUMENTS 6,372,714 B1 * 4/2002 Tanaka .......................... 514/2

FOREIGN PATENT DOCUMENTS

| JP | 2-135092 | 5/1990 |
| WO | WO 95/17373 | 6/1995 |
| WO | WO 96/32102 | 10/1996 |

OTHER PUBLICATIONS

Abstract of the 49$^{th}$ Lecture Meeting of Japan Society of Obstetrics and Gynecology w/English Translation, published on Feb. 20, 1997, p. 394.

* cited by examiner

Primary Examiner—Dave T. Nguyen
Assistant Examiner—Richard Schnizer
(74) Attorney, Agent, or Firm—Oblon, Spivak, McClelland, Maier & Neustadt, P.C.

(57) ABSTRACT

The present invention is directed to a composition for gene transfer which composition contains a quaternary ammonium salt represented by formula (1):

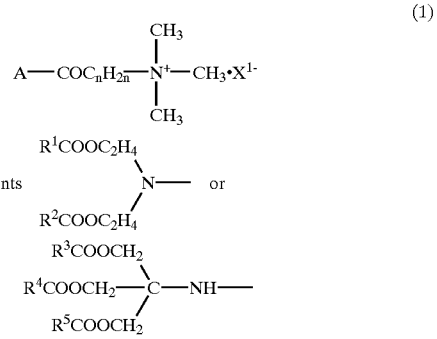

(wherein each of R$^1$, R$^2$, R$^3$, R$^4$, and R$^5$, which are identical to or different from one another, represents a C9–C17 aliphatic group); X$^1$ represents a halogen atom; and n is an integer from 1 to 10 inclusive; and a method for introducing a gene into a cell by use of the composition.

The composition enables effective delivery and expression of a gene which previously could not be effectively expressed in cells due to the low ratio at which the gene is delivered into cells. Therefore, the composition is advantageously used as a gene transfer reagent or a pharmaceutical.

32 Claims, No Drawings

COMPOSITION FOR POLYPEPTIDE TRANSFER TO CELLS

This application is a Division of U.S. application Ser. No. 09/402,452, filed on Oct. 7, 1999, now U.S. Pat. No. 6,372,714, which is a 371 of PCT/JP98/00685, filed Feb. 19, 1998 issued on Apr. 16, 2002.

TECHNICAL FIELD

The present invention relates to a composition for gene transfer into cells, as well as to a method for gene transfer into cells by use of the composition.

BACKGROUND ART

Plasma membranes have low permeability to some compounds which are used as drugs, and thus the drugs fail to exhibit sufficient intracellular pharmacological effect. Low plasma membrane permeability may be attributable to, for example, the compound having low lipid solubility or high molecular weight. A typical example of such a compound to which plasma membranes exhibit low permeability is a gene.

At present, therapeutic treatment by use of such drugs to which plasma membranes exhibit low permeability, in particular, a gene, is conducted by way of injection, etc. However, the permeation of such a drug into the inside of cells is so poor that it is unable to provide satisfactory therapeutic effect.

To solve this problem, there have been proposed various conventional techniques known as drug delivery systems (DDS). As such systems there are, for example, liposomes formed primarily of phospholipids, emulsions composed of surfactants and oils such as soybean oil, mixed micelles made of lipids and surfactants, and microcapsules/microspheres made of biodegradable or non-degradable polymers. However, the conventional techniques have failed to increase permeability of a drug through the membrane; rather, in vitro evaluation has revealed that conventional drug delivery systems have an effect of decreasing cell-membrane permeability of a drug. This is because the drug itself is encapsulated in the drug delivery system, and release of the drug from the system serves as a determining factor. Despite this drawback, drug delivery systems have been attracting close attention, and have been applied to many drugs. This is because when a drug is encapsulated in a drug delivery system, in vivo degradation of the drug can be suppressed, and in vivo kinetics of the drug can be controlled, thus eventually increasing the in vivo drug concentration in the vicinity of the target tissue or cells. Even in the case of liposomes, one of the typical drug delivery systems, although suppression of drug degradation and controlling the in vivo kinetics can both be achieved with relative ease, particles of liposomes ultimately accumulate in the vicinity of the target tissue or cells at high concentration and release the drug, and the remainder of the drug delivery steps depend solely on the permeability of the drug through the plasma membrane. Thus, although liposomes can attain an increased drug concentration near target cells, they have no effect on the permeability of the drug through the plasma membrane.

In some in vitro cases, a drug delivery system increases the rate of drug delivery into cells. Example cases include use of phagocytic cells such as macrophages and monocytes. Phagocytic cells readily ingest microparticles, such as liposomes, by endocytosis, and therefore, transferability of the drug into cells may be increased if the drug is encapsulated in a drug delivery system rather than administered alone. In this case, permeability of the drug through the plasma membrane is not increased. However, if the drug can be temporarily incorporated into cellular vesicles, such as endosomes and lysosomes, together with the drug delivery system and happens to be stable in these microenvironments, the drug can further enter the cytoplasm, resulting in increased drug transferability into cells.

Also, in recent years, extensive research has been directed to gene transfer into non-phagocytic cells, which is achieved through formation of a complex with a gene and cationic lipids (or liposomes containing the cationic lipids) or through encapsulation of a gene into liposomes containing the cationic lipids, thereby allowing the gene to be expressed within the cells. Even though almost nothing is known about the gene transfer mechanism into cells, reagents related to the above-described research are widely commercialized (including reagents such as lipofectAMINE, lipofectACE, lipofectin, transfectam, and genetransfer). Presently, biological researchers are using these reagents on a daily basis as very useful tools for gene transfer into cells, and this method serves as a substitute for the virus and microinjection methods. However, these commercialized reagents have many drawbacks as described in the following a) to d). a) These reagents, as commercialized products, are not stable, and thus are not suitable for storage. Many of these commercialized products are sold in the form of a dispersion in water, and the pH of their aqueous solvents are usually very low pH (for example, the pH is 3.5 for lipofectAMINE and lipofectACE, and 4.3 for lipofectin). Because of this low pH, lipids tend to degrade during storage. It has often been pointed out that efficiencies of gene transfer into cells and of gene expression by use of liposomes, etc. do not have satisfactory reproducibility. One reason for this is the inherent instability of the products. (b) Another drawback is that those products are very unstable in the presence of fetal bovine serum added to a medium for cell culture. As a matter of fact, the commercialized products employ the following protocol for gene transfer: Before gene transfer, the cultured medium containing fetal bovine serum is replaced with serum-free medium; and then, after completion of the gene transfer, the serum-free medium is replaced by serum-containing medium. Recently, it has become clear that these commercialized products are also very unstable in blood as well as in vivo. (c) A further drawback is that those commercialized products are not suitably designed for easy handling. Many of the commercialized products, such as lipofectAMINE, lipofectACE, and lipofectin, are provided in the form of a dispersion in water. For gene delivery, aqueous solvents that contain gene samples are added to these products. However, this protocol only allows the products to form complexes with the genes where genes bind only to the outside of the liposomes. Therefore, these products cannot yield vesicles having the genes encapsulated inside the liposomes. (d) Moreover, a further drawback is very strong cytotoxicity originated from those products. As is well known, the primary purpose for which biological researchers use these commercialized gene transfer reagents is to obtain the cells that have been transformed with exogenous genes and are capable of expressing those genes, and to subsequently use the obtained cells in subsequent studies. For such a purpose, in most cases, whether or not a minor portion of cell population dies during the gene transfer step is immaterial, so long as such transformed cells can be obtained. Thus, there have been commercialized some reagents making use of cationic lipids alone or in combination with liposomes, for delivering into cells a drug such as gene which in nature cannot be permeated through the membrane. However, those commercialized reagents involve many problems, as mentioned above. Thus, it is no exaggeration to say that application of such reagents to human use (such as gene therapy) is unthinkable at present. (Note: Gene therapy includes ex vivo and in vivo methods. In the case of ex vivo treatment, in which cells are taken out of a patient, treated in vitro, and subsequently returned to the patient, cytotoxicity raises a great problem.)

As pointed out above, it would be no exaggeration to conclude that there is no conventional satisfactory method whereby a gene which, except for special cases such as the case of phagocytic cells or some commercially available gene transfer reagents, is poorly permeated through the plasma membrane, is poorly delivered into the inside of cells, or encounters difficulty in manifesting its activity inside the cells can be delivered into cells, after which the gene is allowed to exert its pharmacological efficacy.

Thus, an object of the present invention is to improve permeation through a plasma membrane, transmembrane delivery, and intracellular expression of a gene, to which the plasma membrane has low permeability, in order to deliver the gene into the inside of cells, or to express the gene within the cells.

DISCLOSURE OF THE INVENTION

In view of the above, the present inventors have performed diligent studies in order to solve the problems involved in delivery of a gene to the inside of cells whose plasma membranes have low permeability to the gene, and further to improve expression of the gene inside the cell. As a result, the inventors have found that administration of a gene together with a quaternary ammonium salt represented by formula (1) to cells leads to efficient gene expression, not only in vitro but also in vivo. The present invention has been achieved on the basis of this finding.

Accordingly, the present invention provides a composition for gene transfer into cells, which composition comprises a quaternary ammonium salt represented by the following formula (1):

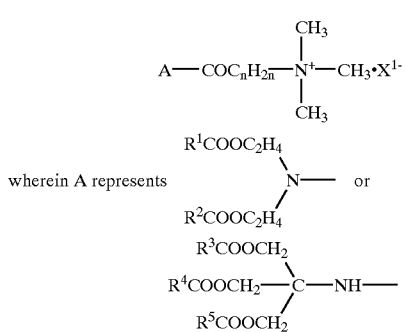

wherein A represents (wherein each of $R^1$, $R^2$, $R^3$, $R^4$, and $R^5$, which are identical to or different from one another, represents a C9–C17 aliphatic group); $X^1$ represents a halogen atom; and n is an integer from 1 to 10 inclusive.

The present invention also provides a composition for gene transfer into cells, which composition comprises a quaternary ammonium salt represented by formula (1) and a gene.

The present invention also provides a gene transfer method comprising applying a composition containing a quaternary ammonium salt represented by formula (1) and a gene into a cell either in vivo or in vitro.

BEST MODE FOR CARRYING OUT THE INVENTION

In formula (1), which represents the quaternary ammonium salt to be incorporated into the composition of the present invention, examples of C9–C17 aliphatic groups represented by $R^1$, $R^2$, $R^3$, $R^4$, and $R^5$ include linear or branched, saturated or unsaturated C9–C17 aliphatic groups. Among them, linear or branched C9–C17 alkyl groups are preferred, and linear or branched C11–C15 alkyl groups are more preferred. Also, C9–C17 linear alkyl groups are more preferred, with C11–C15 linear alkyl groups being particularly preferred. Specifically, undecyl, tridecyl, and pentadecyl linear alkyl groups are particularly preferred. $R^1$, $R^2$, $R^3$, $R^4$, and $R^5$ may be identical to or different from one another. However, identical groups are preferred from the point of view of manufacturing.

In formula (1), the halogen atom represented by $X^1$ is not particularly limited. However, chlorine or bromine is preferred.

In formula (1), n represents an integer from 1 to 10 inclusive. Among such integers, 1 and 10 are particularly preferred. When n is 1, A is preferably

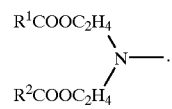

Also, when n is 10, A is preferably

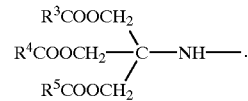

In the composition for gene transfer according to the present invention, the amount of the quaternary ammonium salt represented by formula (1) varies in accordance with the gene employed, use of the composition, and the physical form of the composition. Basically, any amount that allows the gene to be transferred into cells is sufficient. For example, the weight ratio of the composition to the gene is preferably 1:1 to 1:1000; more preferably 1:1–1:100.

Genes used in the present invention may be in the form of either oligonucleotides, DNA, or RNA. In particular, genes resulting in transformation upon in vitro gene transfer and those becoming active upon in viva gene expression are preferred. Examples for the latter case of in viva expression include those for gene therapy and breeding of industrial animals, such as domestic animals and animals for experimental use. When genes used for gene therapy are incorporated into the composition of the present invention, the composition serves as a pharmaceutical composition. Examples of genes for such gene therapy include antisense oligonucleotides, antisense DNA, antisense RNA, and genes encoding physiologically active proteins such as enzymes and cytokines. When genes encoding a certain enzyme are used, a substance that exhibits pharmacological effect due to the action of the enzyme may be used in combination with such genes. For example, tumors may be treated by first delivering a thymidine kinase gene in advance and causing expression in vivo (in tumors), and subsequently administered acyclovir can kill the tumors.

In order to improve the efficiency of gene transfer, the composition of the present invention may further contain phospholipids and/or cholesterol. Examples of phospholipids which may be contained include phosphatidylethanolamine, phosphatidylcholine, phosphatidylserine, phosphatidylinositol, phosphatidylglycerol, cardiolipin, sphingomyelin, plasmalogen, and phosphatidic acid. These phospholipids may be used singly or in combination. Preferably, phosphatidylethanolamine and phosphatidylcholine are used singly or in combination of two or more species; and use of phosphatidylethanolamine is particularly preferred. Fatty acid residues of these phospholipids are not particularly limited. Preferable fatty acid residues include C12–C18 saturated or unsaturated fatty acid residues; and the palmitoyl group, oleoyl group, stearoyl group, and linoleyl group are most preferred. The amount of the phospholipid to be incorporated into the composition of the present invention is preferably 0–80%, more preferably 10–70%, particularly preferably 25–70% based on the mole fraction. In the case of cholesterol, the amount is preferably 0–70%, more preferably 10–60%, particularly preferably 20–50%, based on the mole fraction.

When the quaternary ammonium salt represented by formula (1) is used together with the phospholipid and/or cholesterol, the efficiency of gene transfer increases significantly as compared with the case of sole use of the quaternary ammonium salt. Particularly, a remarkable increase in efficiency is observed when the phospholipid and the quaternary ammonium salt represented by formula (1) are used in combination. Also, in formula (1), when A is a quaternary ammonium salt represented by

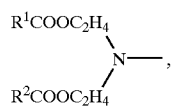

use in combination with phospholipid provides a remarkable increase in the efficiency of gene transfer.

The amount of the quaternary ammonium salt to be incorporated into the composition of the present invention is, based on the mole fraction, preferably 5–100%, more preferably 10–75%, particularly preferably 15–50%.

When the composition of the present invention contains the quaternary ammonium salt, and phospholipid or cholesterol, the mole ratio of the quaternary ammonium salt to the phospholipid or cholesterol is preferably 1:9–9:1, more preferably 2:8–8:2, particularly preferably 3:7–7:3. In this case, one type of phospholipid or a mixture of two or more types of phospholipid can be used.

When the composition of the present invention contains the quaternary ammonium salt, phospholipid, and cholesterol, the mole ratio of the mixture of the quaternary ammonium salt and phospholipid to the cholesterol is preferably 3:7–9:1, more preferably 4:6–9:1, particularly preferably 5:5–8:2. In this case, one type of phospholipid or a mixture of two or more types of phospholipid can be used.

Further, lipid-soluble vitamins such as vitamin E can be incorporated into the composition of the present invention.

With regard to the mode of the composition of the present invention, the quaternary ammonium salt (1) can be incorporated alone or can simply be mixed with the phospholipid and/or cholesterol. Also, in order to form a phospholipid membrane structure, the quaternary ammonium salt (1) can be incorporated alone or can be incorporated in combination with the phospholipid and/or cholesterol. Although no particular limitation is imposed on the modes and manufacturing methods for the lipid membrane structure, examples thereof include a dried lipid mixture, a lipid mixture dispersed in an aqueous solvent, a lipid mixture dispersed in an aqueous solvent and further dried, and a lipid mixture dispersed in an aqueous solvent and then frozen.

Concerning the method of manufacturing the dried lipid mixture, for example, lipid components to be used for the mixture are first dissolved with an organic solvent such as chloroform, and subsequently subjected to in vacuo drying by use of an evaporator or to spray-drying by use of a spray-dryer.

With regard to the dispersion mode in an aqueous solvent, though no particular limitation is imposed on the lipid membrane structure, examples thereof include multilamellar liposome, unilamellar liposome, O/W emulsion, W/O/W emulsion, spherical micelle, and string-shaped micelle, as well as an amorphous multi-layered structure. Although no particular limitation is imposed on the particle size of the lipid membrane structure, the diameter of the liposomes and emulsions is 50 nm to several μm, and that of the spherical micelle is 5 nm to 50 nm. However, in the case in which the concept of a diameter cannot be applied to the string-shaped micelle and amorphous multilayer structure, the concept of the thickness of one layer can be employed, which is 5 nm to 10 nm, and layers are stacked one on another, thus forming the amorphous multilayer structure.

No particular limitation is imposed on the aqueous solvent. However, in addition to water, examples thereof include the following: sugar solutions such as those containing glucose, lactose, or sucrose; polyalcohol solutions such as those containing glycerin or propylene glycol; physiological saline; buffered solutions such as phosphate-buffered solutions, citrate-buffered solutions, and phosphate-buffered physiological saline; and media for cell culture. In order to effect long-term stable preservation of lipid membrane structure in the dispersion mode in an aqueous solvent, the following points are important: from the physical viewpoint, such as prevention of aggregation, electrolytes are eliminated from the aqueous solvent to the greatest possible extent; and from the viewpoint of lipid chemical stability, the pH of the aqueous solvent is set to a range from weak acidity to neutral (pH 3.0–8.0) and dissolved oxygen is removed from the solvent by means of bubbling with nitrogen. Further, use of sugar solutions for preservation of lyophilized samples and spray-dried samples, as well as use of sugar solutions and polyalcohol solutions for cryopreservation, can achieve effective preservation.

Although no particular limitation is imposed on the concentrations of such aqueous solvents, sugar solutions preferably have concentrations of 2–20% (W/V) more preferably 5–10% (W/V); polyalcohol solutions preferably have concentrations of 1–5% (W/V), more preferably 2–2.5% (W/V); and buffered solutions preferably have concentrations of 5–50 mM, more preferably 10–20 mM.

Also, no particular limitation is imposed on concentrations of the lipids forming the lipid membrane structure in the aqueous solvent. The total lipid concentration of the quaternary ammonium salt (1), phospholipid, and cholesterol used for the lipid membrane structure is preferably 0.001 mM-100 mM, more preferably 0.01 mM–20 mM.

In order to manufacture the dispersion mode of the lipid membrane structure in the aqueous solvent, an aqueous solvent is added to the above-described dried lipid mixture, followed by emulsification by use of an ultrasonic homogenizer, a high-pressure jet homogenizer, or an emulsifier such as a homogenizer. Alternatively, without use of such dried lipid mixtures, a well-known liposome manufacturing method such as the reverse-phase evaporation method can be used, and no particular limitation is imposed on such manufacturing methods. In order to control the particle size, extrusion can be carried out under high pressure through a membrane filter having a uniform pore size.

Further, examples of the methods of drying the lipid membrane structure dispersed in an aqueous solvent include typical lyophilization and spray drying. Concerning the aqueous solvent for this purpose, as mentioned above, sugar solutions such as a sucrose or lactose water solution are preferred. Among the merits for further drying the lipid membrane structure already manufactured, such dried forms allow long-term preservation of the lipid membrane structure. Additionally, when gene-containing solutions are added to the dried forms, the lipid membrane structure is efficiently rehydrated so that the gene is also effectively retained by the lipids forming the lipid membrane structure such as liposomes.

A conventional method may be used for further freezing the dispersion mode of the lipid membrane structure in the aqueous solvent. As described above, this method preferably employs aqueous solvents such as a sugar solution or a polyalcohol solution. The merits of further freezing the lipid membrane structure include permitting long-term preservation of the lipid membrane structure.

The composition of the present invention which contains a gene (gene-containing composition) will next be described.

The mode of the gene-containing composition of the present invention may be a mixture of quaternary ammonium salt (1) and a gene; a mixture of quaternary ammonium salt (1), a gene, and phospholipid and/or cholesterol; a mixture of a gene and a lipid membrane structure formed of quaternary ammonium salt (1) alone or in combination with phospholipid and/or cholesterol; or a form in which a gene is carried on the lipid membrane structure. Here, "carry" indicates that the gene is buried in the lipid membrane, present on the surface of the lipid membrane, present inside the membrane, buried in a lipid layer, or present on the lipid layer.

As is the case with the lipid membrane structure, no particular limitation is imposed on the form and production method of the gene-containing composition. For example, the composition may be formed into a dry mixture, a dispersion in an aqueous solvent, or a dry or frozen form of the dispersion.

The dry mixture of a lipid and a gene may be prepared by means of, for example, dissolving a lipid component and a gene in an organic solvent such as chloroform, and subsequently subjecting the solution to vacuum drying by use of an evaporator or to spray-drying by use of a spray dryer.

Non-limiting examples of the dispersion of the mixture of a lipid membrane structure and a gene in an aqueous solvent include multilamellar liposome, unilamellar liposome, O/W emulsion, W/O/W emulsion, spherical micelle, string-shaped micelle, or an amorphous multi-layered structure. No particular limitation is imposed on the particle size of the mixture, the composition of the aqueous solvent, or the concentration of the mixture in the aqueous solvent.

Aqueous dispersions of a mixture of the lipid membrane structure and a gene may be prepared through several methods having different characteristic features, yielding different forms of the resulting mixtures of the lipid membrane structure and gene.

According to the first manufacturing method, an aqueous solvent is first added to the above-mentioned dry mixture of lipid and gene, followed by emulsification by use of a commonly-employed emulsifier such as a homogenizer, ultrasonic emulsifier, or a high-pressure jet homogenizer. In order to control the particle size, extrusion may be carried out under high pressure through use of a membrane filter having a uniform pore size. In this case, in order to prepare the dry mixture of lipid and gene, the gene must first be dissolved in an organic solvent. This method is advantageous in that interaction between the gene and the lipid membrane structure can be fully utilized, so that the gene can enter the inside of the multi-layer when the lipid membrane structure has a layered structure. Thus, in general, the method enables more genes to be carried by the lipid membrane structure.

According to the second manufacturing method, after lipid components are dissolved in an organic solvent, the organic solvent is removed so as to obtain a dry material. Then, an aqueous solvent that contains a gene is added to the dry material, followed by emulsification. In order to control the particle size, extrusion can be carried out under high pressure through a membrane filter having a uniform pore size. This method can be applied to genes that are difficult to dissolve in an organic solvent but are easily dissolved in an aqueous solvent. This method is advantageous in that genes can be retained by the inner aqueous phase of liposomes.

According to the third manufacturing method, an aqueous solvent that contains a gene is added to lipid membrane structures (such as liposomes, emulsions, micelles, or layered structures) which has already been dispersed in another aqueous solvent. Therefore, this method is only applied to water-soluble genes. Further, by this method, genes are later added separately to the lipid membrane structure that has been prepared in advance. Because of this, if the gene is large in size, it is unable to enter the inside of the lipid membrane structure and only binds to the surface thereof. When liposomes are used as the lipid membrane structure, this third method is known to provide a sandwich structure in which the gene is sandwiched by liposomal particles (generally called a complex). The merit to this third method is that the lipid membrane structure, such as that of the liposomes, emulsions, micelles, and layered structures, dispersed in an aqueous solvent can be stored after manufacturing, and can be used not only for one type of gene but also commonly used for other types of gene. Further, when this method is used, the dispersion containing only the lipid membrane structure is prepared in advance. Because of this, there is no need to consider degradation of drug during emulsification. Also, particle size can be easily controlled. Thus, this manufacturing method is more easily carried out than are the first and second methods.

According to the fourth manufacturing method, a lipid membrane structure is first dispersed in an aqueous solvent, followed by drying. An aqueous solvent that contains a gene is added to the dried material. As is the case with the third manufacturing method, this method can be applied only to water-soluble genes. However, the third and fourth manufacturing methods clearly differ in the state of the lipid membrane structure and gene. In the case of the fourth manufacturing method, first a lipid membrane structure dispersed in an aqueous solvent is prepared, followed by drying to obtain dried materials. After this step, the lipid membrane structure exists in a solid state as fragments of the lipid membrane. As mentioned above, obtaining such solid state lipid fragments requires use of an aqueous sugar solution, preferably a sucrose or lactose solution, serving as an aqueous solvent. When an aqueous solvent that contains a gene is added to the solid state lipid fragments, they are quickly hydrated to reconstitute the lipid membrane structure, as water is absorbed. At this point, the resulting composition that retains the genes inside the lipid membrane structure is generated. In contrast, in the case of the third manufacturing method, when the gene is large in size, it is unable to enter the inside of the lipid membrane structure and only binds to its surface. One advantage of the fourth manufacturing method is that once the materials are manufactured, they can be used not only for one type of gene but also commonly for other types of genes. Another advantage is that since the aqueous dispersion containing the lipid membrane structure alone is prepared in advance, degradation of the drug during emulsification is not a consideration. Further, the particle size can be easily controlled. Thus, this manufacturing method is more easily carried out than are the first and second methods. In addition, since the product is prepared by means of lyophilization or spray-drying, its storage stability is reliably ensured, enabling use as a commercial product; after rehydration of the dry product by use of a gene-containing solution, the particle size is restored to the original size, and even the large gene can be easily retained inside the lipid membrane structure.

Concerning other methods for preparing the dispersion mode of the mixture of the lipid membrane structure and a gene, a well-known method for preparation of liposomes such as the reversed-phase evaporation method can be used. In order to control the particle size, extrusion can be carried out under high pressure through a membrane filter having a uniform pore size. Example methods of drying the above-mentioned mixture of the lipid membrane structure and genes dispersed in the aqueous solvent include lyophilization and spray drying. For this aqueous solvent, as is the case with use of the lipid membrane structure alone, a sugar solution, preferably a sucrose or lactose solution, is used.

Conventional freezing methods may be used for freezing the above-mentioned dispersed mixture of the lipid membrane structure and gene in an aqueous solvent. This aqueous solvent is preferably a sugar or polyalcohol solution, as is the case with the lipid membrane structure alone.

The composition of the present invention can be applied not only to genes but also to other drugs having very low lipid solubility and reagents which are difficult to be delivered into cells, such as physiologically active peptides of high molecular weight and proteins.

By use of the composition of the present invention, genes can be efficiently transferred into cells either in vivo or in vitro. In the case of in vitro transfer, genes can be delivered into target cells by means of adding the composition of the present invention to a suspension containing target cells, or by culturing target cells with medium containing the composition of the present invention. In the case of in vivo transfer, the composition of the present invention can be administered into a host. Administration can be carried out either orally or parentally. Oral administration may be carried out by use of conventional formulations therefor, such as tablets, powders, and granules. Parental administration may be carried out by use of conventional formulations therefor, such as injection, instillation, ointments, and suppositories. Among these, parenteral administration is preferred; particularly, injection is most preferred; and for its administration, intravenous injection or local injection at target cell sites or organs is preferred.

EXAMPLES

Next, the present invention will be described in detail by way of examples, which should not be construed as limiting the invention.

Example 1

Production of Empty Liposomes Without a Gene 1-1. Production of Empty-Liposomes Dispersion Predetermined amounts of a quaternary ammonium salt, phospholipid, and cholesterol were dissolved in chloroform, and subsequently subjected to vacuum drying so as to obtain a lipid mixture. To the mixture, a predetermined amount of isotonic sucrose or lactose solution was added, and subsequently, while being warmed up, the mixture was subjected to emulsification by use of a homomixer. Thus, a crude liposomal dispersion was obtained. Next, in order to adjust the particle size of the liposomes, the liposome solution was subjected to extrusion procedure under high pressure through a membrane filter having a pore size of 0.22 $\mu$m, to thereby obtain an empty-liposome dispersion.

1-2. Production of Lyophilized Empty Liposomes

A predetermined amount of the empty-liposome dispersion prepared in 1-1 was aliquoted into vials, followed by lyophilization, to thereby obtain lyophilized liposomes.

Example 2

Production of Gene-Containing Liposomes 2-1. Production of a Gene-Containing Liposomal Dispersion (Type 1)

An empty-liposome dispersion (2 $\mu$mol/ml of the total lipid concentration) manufactured in 1-1 was diluted with serum-free medium (D-MEM) to a concentration of 100 nmol/ml (the quaternary ammonium salt concentration). Next, 100 $\mu$l of the empty-liposome dispersion, which contained 10 nmol of the quaternary ammonium salt, and 14 $\mu$g DNA (either PGV-C (luciferase gene) or pCAG-lacZ ($\beta$-galactosidase gene)) were mixed with 100 $\mu$l D-MEM and left for 15 min; and then 0.8 ml serum-free D-MEM supplemented with 12.5% FBS (the final concentration of FBS was 10%) was added to the mixture so as to obtain a 1-ml sample.

2-2. Production of a Gene-Containing Liposomal Dispersion (Type 2)

The lyophilized dispersion of empty liposomes containing a concentration equivalent to a 2 $\mu$mol/ml total lipid concentration, which was manufactured in 1-2, was rehydrated with distilled water to thereby reconstitute the original form (2 $\mu$mol/ml as a total lipid concentration). Further, this solution was diluted with serum-free medium (D-MEM) to 100 nmol/ml as a quaternary ammonium salt concentration. Next, 100 $\mu$l of this liposomal dispersion containing a 100 nmol equivalent quaternary ammonium salt and 1 $\mu$g DNA (PGV-C or pCAG-lacZ) was mixed with 100 $\mu$l serum-free medium (D-MEM), and left for 15 min. Further, to the mixture, 0.8 ml D-MEM supplemented with 12.5% FBS (the final concentration of FBS was 10%) was added to obtain 1 ml of solution to thereby obtain a sample 2-3. Production of a Gene-Containing Liposome Dispersion (Type 3)

Distilled water that containing DNA (PGV-C or pCAG-lacZ) was added for rehydration (1 $\mu$g DNA/10 nmol of the quaternary ammonium salt) to the lyophilized empty liposomes manufactured in 1-2 (2 $\mu$mol/ml equivalent as the total lipid concentration), and left for 15 min. Then the mixture was diluted to a final concentration of 1 $\mu$g/ml DNA with D-MEM supplemented with 10% FBS to thereby obtain a sample.

2-4. Production of a Gene-Containing Liposomal Dispersion (Type 4)

The empty liposomal dispersion manufactured in 1-1 (2 $\mu$mol/ml as the total lipid concentration) was diluted to 400 nmol/ml as the quaternary ammonium salt with serum-free medium (D-MEM). Next, 500 µl of this liposomal dispersion, containing 200 nmol of the quaternary ammonium salt, and 500 µl of serum-free medium (D-MEM) containing 20 µg DNA (pCAG-lacZ) were mixed, and left for 5 min., to thereby obtain a sample.

2-5. Production of a Gene-Containing Liposomal Dispersion (Type 5)

To the lyophilized empty liposomes equivalent to 2 µmol/ml of the total lipid and manufactured in 1-2, distilled water was added for rehydration to thereby reconstitute the original form (2 µmol/ml of the total lipid concentration), and the solution was further diluted with serum-free medium (D-MEM) so as to adjust the concentration to 400 nmol/ml as the quaternary ammonium salt. Next, 500 µl of this liposomal dispersion, containing 200 nmol of the quaternary ammonium salt, and 500 µl of serum-free medium (D-MEM) containing 20 µg DNA (pCAG-lacZ) were mixed and left for 5 min, to thereby obtain a sample.

2-6. Production of a Gene-Containing Liposomal Dispersion (Type 6)

To the lyophilized empty liposomes equivalent to 2 µmol/ml of the total lipid and manufactured in 1-2, distilled water containing DNA (pCAG-lacZ) was added (1 µg DNA/10 nmol of the quaternary ammonium salt) for rehydration, and left for 15 min. Further, this liposomal dispersion was diluted to a final concentration of 20 µg/ml DNA with serum-free medium (D-MEM), to thereby obtain a sample.

2-7. Production of a Gene-Containing Liposomal Dispersion (Type 7)

pCAG-lacZ DNA contained in the sample of the gene-containing liposomal dispersion (type 5) manufactured in 2-5 was replaced with pCAG-TK (a thymidine kinase gene).

In all other respects, the type 7 sample was manufactured in the same manner as was the type 5 sample.

Test Example 1

Measurement of Luciferase Activity

Respective types of tumor cells were plated onto 6-well plates at a concentration of $1 \times 10^5$–$8 \times 10^5$ cells/well, and cultured for 24 h in medium supplemented with 10% FBS, after which each well was washed once with serum-free medium. Then, 1 ml of the liposomal dispersion containing-PGV-C (see 2-1, 2-2, and 2-3; the final concentration was 1 µg DNA/10 nmol of the quaternary ammonium salt/ml) was added to each well, and reacted at 37° C. for 5 h. Then, after each well was washed with serum-free medium once, culture medium supplemented with 10% FBS was added to each well; and, after cells were further cultured for 2 days, luciferase assay was carried out.

Luciferase assay was performed as described below. Each well was washed twice with phosphate-buffered saline (−) [PBS (−)]. Then, 150 µl of a cell-solubilizing solution (LCβ) was added to each well, and the well plates were left at room temperature for 15 min. Then the cells were scraped off from the plate substrate by use of a cell scraper. Each lysate was subjected to centrifugation at 12,000 rpm for 2 min. Upon mixing 20 µl of the supernatant with 100 µl of a luminescent reagent, luminescence was measured by use of a lumi photometer (TD-4000, Laboscience). The amount of protein in each sample was estimated by use of BCA Protein Assay Reagent. Luciferase activity was expressed as emitted amount/mg protein. The results are shown in Tables 1 and 2.

TABLE 1

In vitro luciferase activity obtained through use of different liposomes (D-MEM medium supplemented with 10% FBS)

| | Composition of liposomal membrane [Cationic lipid appears first] [Membrane composition props. in Exs. are on the mole basis.] | Remarks | Method for preparing a liposomal disper-sion containing a gene | Luciferase activity (light units/mg protein sec) | | | | |
|---|---|---|---|---|---|---|---|---|
| | | | | Colo320 (colon cancer) | mEIIL (uterus cancer) | HEC-1A (uterus cancer) | HRA (ovary cancer) | ES-2 (ovary cancer) |
| Comp. Ex. 1 | Commercial Genetransfer (Wako Pure Chemicals) | Compositional prop. of the membrane;[1] | lipid film[7] | 489 | 838 | 3185 | 643 | 245 |
| Comp. Ex. 2 | Commercial LipofectACE (Life Technologies) | Compositional prop. of the membrane;[2] | complex[8] | 176 | | 3933 | 944 | |
| Comp. Ex. 3 | Commercial LipofectAMINE (Life Technologies) | Compositional prop. of the membrane;[3] | Complex | | | | 429 | |
| Comp. Ex. 4 | Commercial LIPOFECTIN (Life Technologies) | Compositional prop. of the membrane;[4] | Complex | | | | 70 | |
| Comp. Ex. 5 | Commercial DMRIE-C (Life Technologies) | Compositional prop. of the membrane;[5] | Complex | | | | 143 | |
| Comp. Ex. 6 | Leaf Huang[a] | Compositional prop. of the membrane;[6] | Complex | 8 | | 6 | 0 | |
| Comp. Ex. 7 | SA[b]/DOPE[c]/DLPC[d] = 2/4/4 | | type 3 | 8 | | 194 | 0 | |
| Comp. Ex. 8 | only DC-6-14[e] | Cationic lipid alone | type 1 | | | | 4 | 0 |
| Ex. 1 | DC-6-12/DOPE = 5/5 | | type 1 | | | | | 869 |
| Ex. 2 | DC-6-14/DOPE = 5/5 | | type 1 | | 2671 | | 4877 | 1237 |
| Ex. 3 | DC-6-16/DOPE = 5/5 | | type 3 | | | | 11823 | 1423 |

TABLE 1-continued

In vitro luciferase activity obtained through use of different liposomes (D-MEM medium supplemented with 10% FBS)

| | Composition of liposomal membrane [Cationic lipid appears first] [Membrane composition props. in Exs. are on the mole basis.] | Remarks | Method for preparing a liposomal disper-sion containing a gene | Luciferase activity (light units/mg protein sec) | | | | |
|---|---|---|---|---|---|---|---|---|
| | | | | Colo320 (colon cancer) | mEIIL (uterus cancer) | HEC-1A (uterus cancer) | HRA (ovary cancer) | ES-2 (ovary cancer) |
| Ex. 4 | DC-6-16/DOPE = 4/6 | | type 3 | 929 | | | | |
| Ex. 5 | DC-6-12/DOPE/Chol$^{f)}$ = 4/3/3 | | type 1 | | | | 1244 | 323 |
| Ex. 6 | DC-6-14/DOPE/Chol = 4/3/3 | | type 1 | | 3096 | 103503 | 71498 | 1682 |
| Ex. 7 | DC-6-14/DOPE/Chol = 4/3/3 | | type 2 | | | 71029 | | |
| Ex. 8 | DC-6-16/DOPE/DLPC = 4/2/4 | | type 1 | | | | 11930 | |
| Ex. 9 | DC-6-14/DOPE/Chol = 2.9/4.2/2.9 | | type 1 | | 466 | | 6111 | 1094 |
| Ex. 10 | DC-6-14/DOPE/Chol = 3.6/3.6/2.8 | | type 1 | | 2455 | | 10776 | 1070 |
| Ex. 11 | DC-6-14/DOPE/Chol = 4.6/1.8/3.6 | | type 1 | | 1607 | | 3161 | 421 |
| Ex. 12 | DC-6-14/DOPE/Chol = 5/2/3 | | type 1 | | 1111 | | 3532 | 261 |
| Ex. 13 | DC-6-16/DOPE/DLPC = 3/4/3 | | type 2 | 469 | | | 629 | |
| Ex. 14 | DC-6-16/DOPE/DLPC = 4/4/2 | | type 2 | 423 | | | 1923 | |
| Ex. 15 | DC-6-18:1/DOPE/DLPC = 2/4/4 | | type 2 | 785 | | | | |
| Ex. 16 | DC-6-18:1/DOPE/Chol = 2/4/4 | | type 2 | 2951 | | | | | prop.: proportion
$^{a)}$See Biochem. Biophys. Res. Comm., vol. 179, No. 1, 280–285 (1991)
$^{b)}$SA: Stearylamine (typical cationic lipid)
$^{c)}$DOPE: Dioleylphosphatidylethanolamine
$^{d)}$DLPC: Dilauroylphosphatidylcholine
$^{e)}$DC-6-12: O,O'-N-didodecanoyl-N-(α-trimethylammonioacetyl)diethanolamine chloride
DC-6-14: O,O'-N-ditetradecanoyl-N-(α-trimethylammonioacetyl)diethanolamine chloride
DC-6-16: O,O'-N-dihexadecanoyl-N-(α-trimethylammonioacetyl)diethanolamine chloride
DC-6-18:1: O,O'-N-dioctadecanoyl-N-(α-trimethylammonioacetyl)diethanolamine chloride
$^{f)}$Chol: cholesterol
$^{1)}$N-[α-trimethylammonioacetyl]-didodecyl-D-glutamate/DOPE/DLPC = 2/4/4 (mole ratio)
$^{2)}$Dimethyloctadecylammonium bromide/DOPE = 2.9/7.1 (weight ratio)
$^{3)}$2,3-Dioleyloxy-N-[2-(sperminecarboxamide)ethyl]-N,N-dimethyl-1-propaneammoniumtrifluoro acetate/DOPE = 3/1 (weight ratio)
$^{4)}$N-[1-(2,3-dioleyloxy)propyl]-n,n,n-trimethylammonium chloride/DOPE = 5/5 (weight ratio)
$^{5)}$1,2-Dimyristyloxypropyl-3-dimethylhydroxyethylammonium bromide/cholesterol = 1/1 (mole ratio)
$^{6)}$3-β-[N-(N',N'-dimethylaminoethane)carbamoyl]-cholesterol/DOPE = 6/4 (mole ratio)
$^{7)}$The commercial product used was a "lipid film." A gene-containing solution (aqueous solvent) was added to the "lipid film" so that 1 μg DNA was contained per 10 nmol of cationic lipid contained in the component, followed by mixing in a vortex mixer, to thereby obtain a gene-containing aqueous liposomal dispersion.
$^{8)}$The commercial product and the method described in the literature: To an aqueous dispersion of empty liposomea (or a lipid membrane structure), a gene-containing solution (aqueous solvent) was added so that 1 μg DNA was contained per 10 nmol of cationic lipid contained in the component, to thereby obtain a dispersion of gene-liposome complex.

TABLE 2

In vitro luciferase activity obtained through use of different liposomes (D-MEM medium supplemented with 10% FBS)

| | Composition of liposomal membrane [Cationic lipid appears first] [Membrane composition props. in Exs. are on the mole basis.] | Remarks | Method for preparing a liposomal dispersion containing a gene | Luciferase activity (light units/mg protein sec) | | | |
|---|---|---|---|---|---|---|---|
| | | | | Colo320 (colon cancer) | HEC-1A (uterus cancer) | HRA (ovary cancer) | KF (ovary cancer) |
| Comp. Ex. 1 | Commercial Genetransfer (Wako Pure Chemicals) | Compositional prop. of the membrane;$^{1)}$ | lipid film$^{7)}$ | 489 | 3185 | 643 | 23 |
| Comp. Ex. 2 | Commercial LipofectACE (Life Technologies) | Compositional prop. of the membrane;$^{2)}$ | complex$^{8)}$ | 176 | 3933 | 944 | |
| Comp. Ex. 3 | Commercial LipofectAMINE (Life Technologies) | Compositional prop. of the membrane;$^{3)}$ | Complex | | | 429 | |
| Comp. Ex. 4 | Commercial LIPOFECTIN (Life Technologies) | Compositional prop. of the membrane;$^{4)}$ | Complex | | | 70 | |
| Comp. Ex. 5 | Commercial DMRIE-C (Life Technologies) | Compositional prop. of the membrane;$^{5)}$ | Complex | | | 143 | |

TABLE 2-continued

In vitro luciferase activity obtained through use of different liposomes (D-MEM medium supplemented with 10% FBS)

| | Composition of liposomal membrane [Cationic lipid appears first] [Membrane composition props. in Exs. are on the mole basis.] | Remarks | Method for preparing a liposomal dispersion containing a gene | Luciferase activity (light units/mg protein sec) | | | |
|---|---|---|---|---|---|---|---|
| | | | | Colo320 (colon cancer) | HEC-1A (uterus cancer) | HRA (ovary cancer) | KF (ovary cancer) |
| Comp. Ex. 6 | Leaf Huang[a)] | Compositional prop. of the membrane;[6)] | Complex | 8 | 6 | 0 | |
| Comp. Ex. 7 | SA[b)]/DOPE[c)]/DLPC[d)] = 2/4/4 | | type 3 | 8 | 194 | 0 | |
| Ex. 17 | TC-1-12[g)]/DOPE = 5/5 | | type 3 | 2887 | | 342 | |
| Ex. 18 | TC-1-12/DOPE/DLPC = 2/4/4 | | type 1 | 8325 | | 6245 | |
| Ex. 19 | TC-1-12/DOPE/DLPC = 3/4/3 | | type 2 | | | 5429 | |
| Ex. 20 | TC-1-12/DOPE/DLPC = 3/4/3 | | type 3 | 3459 | | 1204 | 40 |
| Ex. 21 | TC-1-12/DOPE/LysoPC[h)] = 2/4/4 | | type 3 | 1598 | | | |
| Ex. 22 | TC-1-12/DOPE/Chol = 5/2.5/2.5 | | type 3 | 2176 | | | |
| Ex. 23 | TC-1-12/DOPE/Chol/DLPC = 2/4/2/2 | | type 3 | | 3909 | | 89 |
| Ex. 24 | TC-1-12/DOPE = 4/6 | | type 2 | 1378 | | | |
| Ex. 25 | TC-1-12/DOPE/DLPC = 4/4/2 | | type 2 | 3355 | 446 | 648 | |
| Ex. 26 | TC-1-12/DOPE/DLPC = 5/4/1 | | type 2 | 2897 | 414 | 488 | |
| Ex. 27 | TC-1-12/DOPE/Lyso-LPC[i)] = 2/4/4 | | type 2 | 4499 | | | |
| Ex. 28 | TC-1-12/DOPE/Lyso-MPC[j)] = 2/4/4 | | type 2 | 3258 | | | |
| Ex. 29 | TC-1-12/DOPE/Chol = 2.5/2.5/5 | | type 2 | 1680 | 223 | | |
| Ex. 30 | TC-1-12/DOPE/Chol = 2.5/5/2.5 | | type 2 | 1606 | 287 | | |
| Ex. 31 | TC-1-12/DOPE/Chol = 5/4.5/0.5 | | type 2 | 1221 | | | | prop.:proportion
[a)–f)] and [1)–8)] See Table 1
[g)] TC-1-12: O,O',O''-tridodecanoyl-N-($\bar{\omega}$-trimethylammoniodecanoyl)-tris(hydroxymethyl)-aminomethane bromide
[h)] LysoPC: Lisophosphatidylcholine
[i)] Lyso-LPC: Lisolauroylphosphatidylcholine
[j)] Lyso-MPC: Lisomyristoylphosphatidylcholine As is apparent from Tables 1 and 2, the gene transfer composition according to the present invention exhibited enhanced gene transfer ability as compared with commercial gene transfer reagents.

Test Example 2

X-gal Staining

Each type of tumor cells were plated in amounts of 1×10⁵–8×10⁵ in a six-well plate, followed by culturing for 24 hours in a medium added with FBS (10%) and washing once with serum-free medium. Subsequently, 1 ml of a gene-containing liposomal dispersion (gene: pCAG-lacZ) prepared in Example 2 (2-1, 2-2, or 2-3; final DNA concentration=1 μg/10 nmol quaternary ammonium salt/ml) was added to each well, and reaction was allowed to proceed for five hours. When five hours have elapsed, the wells were washed once with serum-free medium. FBS (10%)-supplemented medium was added and subjected to incubation for two days, and then X-gal staining.

X-gal staining was performed as follows. Briefly, the sample was washed once with PBS(−), then fixed for 3–4 minutes by use of PBS(−) containing 1% formaldehyde, 0.2% glutaraldehyde, and 0.02% NP40, followed by washing PBS(−) three times, each for 10 minutes. Ultimately, staining was performed for 5–8 hours at 37° C. by use of a mixture solution containing 5 mM $K_4[Fe(CN)_6]$, 5 mM $K_3[Fe(CN)_6]$, 0.01% sodium deoxycholic acid, 0.02% NP40, 2 mM $MgCl_2$, and 0.1% X-gal. Under a microscope, cells were counted at least 1,000 in number, to thereby obtain a Lac Z-positive number. The results are shown in Tables 3 through 5.

TABLE 3

Percentage in vitro LacZ positive cells obtained through use of different liposomes (in medium supplemented with 10% FBS)

| | Composition of liposomal membrane [CL appears first] [MCP in Exs. are on the mole basis.] | Remarks | Method for preparing a lipsomal dispersion containing a gene | Percentage LacZ positive cells (count of positive cells per 100 cells) | | | | | | |
|---|---|---|---|---|---|---|---|---|---|---|
| | | | | HEC-1A (uterus cancer) | mEIIL (uterus cancer) | HRA (ovary cancer) | ES-2 (ovary cancer) | SW626 (ovary cancer) | KF (ovary cancer) | KOC-3S (ovary cancer) |
| Comp. Ex. 1 | Commercial Genetransfer | CP of membrane;[1)] | lipid film[4)] | 2.6 | 7.6 | 10.1 | 8.6 | 9.2 | 3.3 | 6.0 |

TABLE 3-continued

Percentage in vitro LacZ positive cells obtained through use
of different liposomes (in medium supplemented with 10% FBS)

| | Composition of liposomal membrane [CL appears first] [MCP in Exs. are on the mole basis.] | Remarks | Method for preparing a liposomal dispersion containing a gene | HEC-1A (uterus cancer) | mEIIL (uterus cancer) | HRA (ovary cancer) | ES-2 (ovary cancer) | SW626 (ovary cancer) | KF (ovary cancer) | KOC-3S (ovary cancer) |
|---|---|---|---|---|---|---|---|---|---|---|
| Comp. Ex. 3 | Commercial LipofectAMINE | CP of membrane;[2] | complex[5] | | 0.6 | 4.7 | 3.3 | | 0 | 2.4 |
| Comp. Ex. 5 | Commercial DMRIE-C | CP of membrane;[3] | Complex | | 4.0 | 1.3 | 10.1 | | 0.6 | 0.5 |
| Ex. 5 | DC-6-12[a]/DOPE[b]/Chol[c] = 4/3/3 | | type 1 | 21.2 | 10.6 | 38.9 | 24.7 | 14.8 | 14.5 | 4.8 |
| Ex. 6 | DC-6-14/DOPE/Chol = 4/3/3 | | type 1 | | | 42.1 | 23.7 | | 16.0 | 5.9 |
| Ex. 32 | DC-6-12/DOPE/Chol = 4/3/3 | | type 3 | 8.7 | | 8.4 | | 9.3 | 13.7 | |
| Ex. 33 | DC-6-14/DOPE/Chol = 1.8/5.4/2.8 | | type 1 | | | 14.9 | 21.4 | | 7.4 | 4.8 |

CL: Cationic lipid
CP: Compositional proportion
MCP: Membrane compositional proportions

TABLE 4

Percentage in vitro LacZ positive cells obtained through use
of different liposomes (in medium supplemented with 10% FBS)

| | Composition of liposomal membrane [CL appears first] [MCP in Exs. are on the mole basis.] | Remarks | Method for preparing a liposomal dispersion containing a gene | Nakajima (ovary cancer) | Nakajima S2 (ovary cancer) | OVHS-1 (ovary cancer) | SKOV-3 (ovary cancer) | KK (ovary cancer) | OVCAR 3 (ovary cancer) | HNOA (ovary cancer) |
|---|---|---|---|---|---|---|---|---|---|---|
| Comp. Ex. 1 | Commercial Genetransfer | CP of membrane;[1] | lipid film | 6.0 | 5.4 | 0.9 | 6.6 | 31.3 | 8.5 | 1.4 |
| Comp. Ex. 3 | Commercial LipofectAMINE | CP of membrane;[2] | Complex | 0.1 | 0.6 | 1.0 | 0.2 | 0 | 0.4 | 0 |
| Comp. Ex. 5 | Commercial DMRIE-C | CP of membrane;[3] | Complex | 0.1 | 1.0 | 0 | 0.2 | 0 | 4.5 | 0 |
| Ex. 5 | DC-6-12[a]/DOPE[b]/Chol[c] = 4/3/3 | | type 1 | 7.4 | 8.6 | | 8.3 | | | |
| Ex. 6 | DC-6-14/DOPE/Chol = 4/3/3 | | type 1 | | 6.5 | | 11.5 | | 12.3 | |
| Ex. 32 | DC-6-12/DOPE/Chol = 4/3/3 | | type 3 | | | | | | | 4.6 |
| Ex. 33 | DC-6-14/DOPE/Chol = 1.8/5.4/2.8 | | type 1 | | 4.4 | 9.1 | 22.2 | | 7.5 | |

CL: Cationic lipid
CP: Compositional proportion
MCP: Membrane compositional proportions

TABLE 5

Percentage in vitro LacZ positive cells obtained through use
of different liposomes (in medium supplemented with 10% FBS)

| | Composition of liposomal membrane [CL appears first] [MCP in Exs. are on the mole basis.] | Remarks | Method for preparing a liposomal dispersion containing a gene | HEC-1A (uterus cancer) | COS-1 (fibroblast cells) |
|---|---|---|---|---|---|
| Comp. Ex. 1 | Commercial Genetransfer (Wako Pure Chemicals) | CP of membrane;[1] | lipid film | 2.6 | |
| Comp. Ex. 3 | Commercial LipofectAMINE (Life Technologies) | CP of membrane;[2] | Complex | | 0 |
| Ex. 20 | TC-1-12[a]/DOPE[b]/DLPC[d] = 3/4/3 | | type 3 | 11.5 | |
| Ex. 23 | TC-1-12/DOPE/Chol[c]/DLPC = 2/4/2/2 | | type 3 | 18.0 | |
| Ex. 34 | TC-1-12/DOPE/DLPC = 2/4/4 | | type 3 | 14.1 | |
| Ex. 35 | TC-1-12/DOPE/Chol = 3/4/3 | | type 1 | | 3.7 |

TABLE 5-continued

Percentage in vitro LacZ positive cells obtained through use of different liposomes (in medium supplemented with 10% FBS)

| | Composition of liposomal membrane [CL appears first] [MCP in Exs. are on the mole basis.] | Remarks | Method for preparing a liposomal dispersion containing a gene | Percentage LacZ positive cells (count of positive cells per 100 cells) | |
|---|---|---|---|---|---|
| | | | | HEC-1A (uterus cancer) | COS-1 (fibroblast cells) |
| Ex. 36 | TC-1-12/DOPE/Chol = 3/4/3 | | type 3 | 11.6 | |
| Ex. 37 | TC-1-12/DOPE/Chol/DLPC = 2/4/3/1 | | type 3 | 15.3 | |

CL: Cationic lipid
CP: Compositional proportion
MCP: Membrane compositional proportions
[a)] DC-6-12: O,O'-N-didodecanoyl-N-(α-trimethylammonioacetyl)diethanolamine chloride
DC-6-14: O,O'-N-ditetradecanoyl-N-(α-trimethylammonioacetyl)diethanolamine chloride
DC-6-16: O,O'-N-dihexadecanoyl-N-(α-trimethylammonioacetyl)diethanolamine chloride
TC-1-12: O,O',O''-tridodecanoyl-N-(ω-trimethylammoniodecanoyl)-tris(hydroxymethyl)-aminomethane bromide
[b)] DOPE: Dioleylphosphatidylethanolamine
[c)] Chol: cholesterol
[d)] DLPC: Dilauroylphosphatidylcholine
[1)] N-[α-trimethylammonioacetyl]-didodecyl-D-glutamate/DOPE/DLPC = 2/4/4 (mole ratio)
[2)] 2,3-Dioleyloxy-N-[2-(sperminecarboxamide)ethyl]-N,N-dimethyl-1-propaneammoniumtrifluoro acetate/DOPE = 3/1 (weight ratio)
[3)] 1,2-dimyristyloxypropyl-3-dimethyl-hydroxyethylammonium bromide/cholesterol = 1/1 (mole ratio)
[4)] The commercial product used was a "lipid film." A gene-containing solution (aqueous solvent) was added to the "lipid film" so that 1 μg DNA was contained per 10 nmol of cationic lipid contained in the component, followed by mixing in a vortex mixer, to thereby obtain a gene-containing aqueous liposomal dispersion.
[5)] The commercial product and the method described in the literature: To an aqueous dispersion of empty liposomes (or a lipid membrane structure), a gene-containing solution (aqueous solvent) was added so that 1 μg DNA was contained per 10 nmol of cationic lipid contained in the component, to thereby obtain a dispersion of gene-liposome complex.

As is apparent from Tables 3 to 5, the gene transfer composition according to the present invention exhibited enhanced gene transfer ability as compared with commercial gene transfer reagents.

Test Example 3

X-gal Staining (2)

Each type of tumor cells were intraperitoneally inoculated to each nude mouse in amounts of $5 \times 10^6$ (mEIIL, ES-2)-$6 \times 10^7$ (HRA). After one day (in the case of HRA), about 10 days (in the case of ES-2), or about 3 weeks (in the case of mEIIL), 1 ml of the gene-containing liposomal dispersion (gene: pCAG-lacZ) described above (2-4, 2-5, or 2-6; final DNA concentration=20 μg/200 nmol quaternary ammonium salt/ml) was intraperitoneally administered to the mouse. On the following day (in the case of mEIIL and HRA) or two days later (in the case of ES-2), tumor cells were collected, and $3 \times 10^5 - 5 \times 10^5$ cells were plated in the wells of a 6-well plate. The cells were incubated for 24 hours by use of a medium supplemented with 10% FBS, followed by X-gal staining. X-gal staining was performed in a manner similar to that in Test Example 2. The results are shown in Table 6.

TABLE 6

Percentage in vivo LacZ positive cells obtained through use of different liposomes

| | | Composition of liposomal membrane [CL appears first] [MCP in Exs. are on the mole basis.] | Remarks | Method for preparing a liposomal dispersion containing a gene | Percentage Lac Z positive cells (count of cells per 100 cells) | | |
|---|---|---|---|---|---|---|---|
| | | | | | HRA (ovary cancer) | mEIIL (uterus cancer) | ES-2 (ovary cancer) |
| Comp. Ex. 1 | Commercial Genetransfer | | CP of membrane;[1)] | Lipid film[6)] | 0.95 | 0.25 | 0.25 |
| Comp. Ex. 2 | Commercial LipofectACE | | CP of membrane;[2)] | complex[7)] | | 0.62 | |
| Comp. Ex. 3 | Commercial LipofectAMINE | | CP of membrane;[3)] | Complex | | 0.23 | |
| Comp. Ex. 4 | Commercial LIPOFECTIN | | CP of membrane;[4)] | Complex | | 0.38 | |
| Comp. Ex. 5 | Commercial DMRIE-C | | CP of membrane;[5)] | Complex | | 1.52 | |
| Ex. 38 | DC-6-12[a)]/DOPE[b)] = 5/5 | | | type 4 | 5.50 | | |
| Ex. 39 | DC-6-14/DOPE = 5/5 | | | type 5 | | 1.08 | |
| Ex. 40 | DC-6-14/DOPE = 5/5 | | | type 6 | | 1.04 | |
| Ex. 41 | DC-6-12/DOPE/Chol[c)] = 4/3/3 | | | type 4 | 4.71 | 1.29 | 2.43 |

TABLE 6-continued

Percentage in vivo LacZ positive cells obtained through use of different liposomes

| | Composition of liposomal membrane [CL appears first] [MCP in Exs. are on the mole basis.] | Remarks | Method for preparing a liposomal dispersion containing a gene | Percentage Lac Z positive cells (count of cells per 100 cells) | | |
|---|---|---|---|---|---|---|
| | | | | HRA (ovary cancer) | mEIIL (uterus cancer) | ES-2 (ovary cancer) |
| Ex. 42 | DC-6-14/DOPE/Chol = 4/3/3 | | type 4 | | 1.32 | |
| Ex. 43 | DC-6-14/DOPE/Chol = 4/3/3 | | type 6 | | 0.96 | |
| Ex. 44 | DC-6-14/DOPE/Chol = 1.8/5.4/2.8 | | type 4 | 4.32 | | |
| Ex. 45 | DC-6-14/DOPE = 4/6 | | type 4 | 6.30 | | |

CL: Cationic lipid
CP: Compositional proportion
MCP: Membrane composition proportions
[a] DC-6-12: O,O'-N-didodecanoyl-N-(α-trimethylammonioacetyl)diethanolamine chloride
DC-6-14: O,O'-N-ditetradecanoyl-N-(α-trimethylammonioacetyl)diethanolamine chloride
[b] DOPE: Dioleylphosphatidylethanolamine
[c] Chol: cholesterol
[1] N-[α-trimethylammonioacetyl]-didodecyl-D-glutamate/DOPE/DLPC = 2/4/4 (mole ratio)
[2] Dimethyloctadecylammonium bromide/DOPE = 2.9/7.1 (weight ratio)
[3] 2,3-Dioleyloxy-N-[2-(sperminecarboxamide)ethyl]-N,N-dimethyl-1-propaneammoniumtrifluoro acetate/DOPE = 3/1 (weight ratio)
[4] N-[1-(2,3-dioleyloxy)propyl]-n,n,n-trimethylammonium chloride/DOPE = 5/5 (weight ratio)
[5] 1,2-dimyristyloxypropyl-3-dimethyl-hydroxyethylammonium bromide/cholesterol = 1/1 (mole ratio)
[6] The commercial product used was a "lipid film." A gene-containing solution (aqueous solvent) was added to the "lipid film" so that 1 μg DNA was contained per 10 nmol of cationic lipid contained in the component, followed by mixing in a vortex mixer, to thereby obtain a gene-containing aqueous liposomal dispersion.
[7] The commercial product and the method described in the literature: To an aqueous dispersion of empty liposomes (or a lipid membrane structure), a gene-containing solution (aqueous solvent) was added so that 1 μg DNA was contained per 10 nmol of cationic lipid contained in the component, to thereby obtain a dispersion of gene-liposome complex.

As is apparent from Table 6, the gene transfer composition according to the present invention exhibited enhanced gene transfer ability as compared with commercial gene transfer reagents.

Test Example 4

Life-Prolonging Effect in Tumor-Bearing Mice

Each type of tumor cells were intraperitoneally inoculated to nude mice in amounts of $3 \times 10^5$ (HRA), $1 \times 10^6$ (mES-2), or $5 \times 10^6$ (day 0). From day 7 (in cases of HRA and ES-2) or from day 10 (in the case of mEIIL), 1 ml of the gene-containing liposomal dispersion (gene: pCAG-TK) described above (2-7; final DNA concentration=20 μg/200 nmol quaternary ammonium salt/ml) was intraperitoneally administered to each mouse. For each of 13 consecutive days starting from day 9, i.e., until day 21 (in cases of HRA and ES-2), or for each of 13 consecutive days starting from day 12, i.e., until day 24 (in the case of mEIIL), acyclovir was intraperitoneally administered to each mouse twice a day at a dose of 35 mg/kg. To mice of a control group, pCAG-lacZ gene was administered in place of pCAG-TK. The significance test employed was the Cox-Mantel method. The results are shown in Table 7.

TABLE 7

Life-prolonging effect of liposomes in a peritoneum-implanted model

| | Composition of liposomal membrane [mole ratio] | Gene | Oncocyte | Count of implanted cells | Number of mice | Days of observation | Days of 50% Survival | Survived mice at the end of observation | Significance test |
|---|---|---|---|---|---|---|---|---|---|
| Ex. 46 | DC-6-14[a]/DOPE[b] = 5/2 | pCAG-TK | HRA | $3 \times 10^5$ | 12 | 70 | 40 | 5 | $p < 0.05$ |
| (C.G.) | DC-6-14/DOPE = 5/2 | pCAG-lacZ | HRA | $3 \times 10^5$ | 12 | 70 | 34 | 1 | |
| Ex. 47 | DC-6-14/DOPE = 5/2 | pCAG-TK | mEIIL | $5 \times 10^6$ | 8 | 85 | 85 or more | 6 | $p < 0.05$ |
| (C.G.) | DC-6-14/DOPE = 5/2 | pCAG-lacZ | mEIIL | $5 \times 10^6$ | 8 | 85 | 67 | 1 | |
| Ex. 48 | DC-6-14/DOPE/Chol[c] = 1.8/5.4/2.8 | pCAG-TK | mEIIL | $5 \times 10^6$ | 8 | 85 | 85 or more | 5 | $p < 0.05$ |
| (C.G.) | DC-6-14/DOPE/Chol = 1.8/5.4/2.8 | pCAG-lacZ | mEIIL | $5 \times 10^6$ | 8 | 85 | 60 | 2 | $p < 0.05$ |
| Ex. 49 | DC-6-12/DOPE/Chol = 4/3/3 | pCAG-TK | ES-2 | $1 \times 10^6$ | 12 | 77 | 50 | 3 | |
| (C.G.) | DC-6-12/DOPE/Chol = 4/3/3 | pCAG-lacZ | ES-2 | $1 \times 10^6$ | 12 | 77 | 37 | 0 | |

C.G.: Control group
[a] DC-6-12: O,O'-N-didodecanoyl-N-(α-trimethylammonioacetyl)diethanolamine chloride
DC-6-14: O,O'-N-ditetradecanoyl-N-(α-trimethylammonioacetyl)diethanolamine chloride
[b] DOPE: Dioleylphosphatidylethanolamine
[c] Chol: cholesterol As is apparent from Table 7, the gene transfer composition according to the present invention exhibited excellent life-prolonging effect.

INDUSTRIAL APPLICABILITY

The composition of the present invention enables effective delivery and expression of a gene which previously could not be effectively expressed in a cell due to the low ratio at which the gene is introduced into cells. Therefore, the composition is advantageously used as a gene transfer reagent or a pharmaceutical.

What is claimed is:

1. The composition for delivering polypeptides into cells, which comprises O,O'-ditetradecanoyl-($\alpha$-trimethylammonioacetyl)diethanolamine halide, one or more phospholipids, cholesterol, and at least one polypeptide.

2. A composition according to claim 1, wherein the one or more phospholipids are selected from the group consisting of phosphatidylethanolamine, phosphatidylcholine, phosphatidylserine, phosphatidylinositol, phosphatidylglycerol, cardiolipin, sphingomyelin, plasmalogen, and phosphatidic acid.

3. The composition according to claim 1, wherein the one or more phospholipids are selected from the group consisting of phosphatidylethanolamine and phosphatidylcholine.

4. The composition according to claim 1, wherein the mole ratio of a mixture of O,O'-ditetradecanoyl-N-($\alpha$-trimethylammonioacetyl)diethanolamine halide and the one or more phospholipids to cholesterol is in the range of 3:7 to 9:1.

5. The composition according to claim 1, which forms liposomes.

6. The composition according to claim 2, wherein the mole ratio of a mixture of O,O'-ditetradecanoyl-N-($\alpha$-trimethylammonioacetyl)diethanolamine halide and the one or more phospholipids to cholesterol is in the range of 3:7 to 9:1.

7. The composition according to claim 3, wherein the mole ratio of a mixture of O,O'-ditetradecanoyl-N-($\alpha$-trimethylammonioacetyl)diethanolamine halide and the one or more phospholipids to cholesterol is in the range of 3:7 to 9:1.

8. The composition according to claim 2, which forms liposomes.

9. The composition according to claim 3, which forms liposomes.

10. The composition according to claim 4, which forms liposomes.

11. The composition according to claim 6, which forms liposomes.

12. The composition according to claim 7, which forms liposomes.

13. A method for delivering polypeptides into cells, comprising applying the composition as recited in claim 1 to the cells in vitro.

14. A method for delivering polypeptides into cells, comprising applying the composition as recited in claim 2 to the cells in vitro.

15. A method for delivering polypeptides into cells, comprising applying the composition as recited in claim 3 to the cells in vitro.

16. A method for delivering polypeptides into cells, comprising applying the composition as recited in claim 4 to the cells in vitro.

17. A method for delivering polypeptides into cells, comprising applying the composition as recited in claim 5 to the cells in vitro.

18. A method for delivering polypeptides into cells, comprising applying the composition as recited in claim 6 to the cells in vitro.

19. A method for delivering polypeptides into cells, comprising applying the composition as recited in claim 7 to the cells in vitro.

20. A method for delivering polypeptides into cells, comprising applying the composition as recited in claim 8 to the cells in vitro.

21. A method for delivering polypeptides into cells, comprising applying the composition as recited in claim 9 to the cells in vitro.

22. A method for delivering polypeptides into cells, comprising applying the composition as recited in claim 10 to the cells in vitro.

23. A method for delivering polypeptides into cells, comprising applying the composition as recited in claim 1 to the cells in vivo.

24. A method for delivering polypeptides into cells, comprising applying the composition as recited in claim 2 to the cells in vivo.

25. A method for delivering polypeptides into cells, comprising applying the composition as recited in claim 3 to the cells in vivo.

26. A method for delivering polypeptides into cells, comprising applying the composition as recited in claim 4 to the cells in vivo.

27. A method for delivering polypeptides into cells, comprising applying the composition as recited in claim 5 to the cells in vivo.

28. A method for delivering polypeptides into cells, comprising applying the composition as recited in claim 6 to the cells in vivo.

29. A method for delivering polypeptides into cells, comprising applying the composition as recited in claim 7 to the cells in vivo.

30. A method for delivering polypeptides into cells, comprising applying the composition as recited in claim 8 to the cells in vivo.

31. A method for delivering polypeptides into cells, comprising applying the composition as recited in claim 9 to the cells in vivo.

32. A method for delivering polypeptides into cells, comprising applying the composition as recited in claim 10 to the cells in vivo.

* * * * *

UNITED STATES PATENT AND TRADEMARK OFFICE
CERTIFICATE OF CORRECTION

PATENT NO.   : 6,613,735 B2
DATED        : September 2, 2003
INVENTOR(S)  : Kenichi Tanaka et al.

It is certified that error appears in the above-identified patent and that said Letters Patent is hereby corrected as shown below:

<u>Column 23,</u>
Line 13, "The composition", should read -- A composition --
Line 18, "A composition", should read -- The composition --

Signed and Sealed this

Fourth Day of November, 2003

JAMES E. ROGAN
*Director of the United States Patent and Trademark Office*